United States Patent

Mine et al.

[11] Patent Number: 5,942,646
[45] Date of Patent: Aug. 24, 1999

[54] OPTICALLY ACTIVE ALCOHOL AND PROCESS FOR THE PRODUCTION THEREOF

[75] Inventors: Takakiyo Mine; Tomoyuki Yui, both of Tsukuba, Japan

[73] Assignee: Mitsubishi Gas Chemical Company, Inc., Tokyo, Japan

[21] Appl. No.: 08/968,261

[22] Filed: Nov. 12, 1997

[30] Foreign Application Priority Data

Nov. 15, 1997 [JP] Japan ..................................... 8-304787

[51] Int. Cl.$^6$ ..................................................... C07C 31/34
[52] U.S. Cl. ........................................... 568/842; 435/157
[58] Field of Search ................................. 568/840, 842, 568/841, 681, 683; 435/157

[56] References Cited

FOREIGN PATENT DOCUMENTS

| | | |
|---|---|---|
| 64-3154 | 1/1989 | Japan . |
| 1316339 | 12/1989 | Japan . |
| 1316367 | 12/1989 | Japan . |
| 1316372 | 12/1989 | Japan . |
| 2225434 | 9/1990 | Japan . |
| 2229128 | 9/1990 | Japan . |
| 2282340 | 11/1990 | Japan . |
| 05051341 | 3/1993 | Japan . |
| 5-65486 | 3/1993 | Japan . |
| 8337555 | 12/1996 | Japan . |

OTHER PUBLICATIONS

Yamaguchi, et al., Kagaku (Chemistry), 42 (11), 757–761 (1987).

Johno, et al., "Ferroelectric Liquid Crystals", Yuki Goseikagaku Kyokai Shi (J. Org. Syn. Chem. Soc.), 47(6), 568–585 (1989).

Lin, et al., "A Microbially Based Approach for the Preparation of Chiral Molecules Possessing the Trifluoromethyl Group", J. Org. Chem., 52, 3211–3217 (1987).

Kirchner, et al., "Resolution of Racemic Mixtures via Lipase Catalysis in Organic Solvents", J. Am. Chem. Soc., 107, 7072–7076 (1985).

*Primary Examiner*—Michael L. Shippen
*Attorney, Agent, or Firm*—Sherman and Shalloway

[57] ABSTRACT

A novel R-configuration or S-configuration optically active alcohol of the formula (1), $$CF_3C^*H(OH)(CH_2)_mOCH_2CH_nF_{3-n} \qquad (1)$$

wherein C* is an asymmetric carbon atom, m is an integer of 2 to 7, and n is an integer of 0 to 2, and a process for the production of the optically active alcohol from a monohalogenated alkyl having a fluoroalkoxy group at a terminal. The novel optically active alcohol, provided by the present invention, having a trifluoromethyl group on an asymmetric carbon atom and a fluoroalkoxy group at a terminal, is useful as a raw material for the production of a novel liquid crystal compound.

10 Claims, No Drawings

OPTICALLY ACTIVE ALCOHOL AND PROCESS FOR THE PRODUCTION THEREOF

FIELD OF THE INVENTION

The present invention relates to a novel optically active secondary alcohol having a trifluoromethyl group on an asymmetric carbon atom and a fluorine-substituted alkoxy group at a terminal, and a process for the production thereof.

PRIOR ART

Optically active compounds have been used in the fields of medicaments and agrochemicals, and in recent years, they attract attention as functional materials for ferroelectric liquid crystals and organic non-linear materials.

For example, in the field of the organic non-linear materials, an asymmetric center is desirably present in the molecule so that an organic material can produce a secondary non-linear optical effect (see, e.g., Yamaguchi, Nakano, Fueno, "KAGAKU (Chemistry)" 42(11), 757 (1987)). Further, in the field of ferrroelectric liquid crystal compound, for a liquid crystal compound to show ferroelectric characteristics, the liquid crystal molecule is required to have an optically active structure (see, e.g., Johne, Fukuda, "YUKI GOSEIKAGAKU KYOKAI SHI (Journal of Organic Synthesis Chemistry Society)", 47(6), 568 (1989)).

In recent years, further, anti-ferroelectric liquid crystal compounds attract remarkable attention, but the liquid crystal molecule of the anti-ferroelectric liquid crystal compound is required to have an optically active structure, like the above ferroelectric liquid crystal compounds.

In the above fields, optically active 2-butanol, 2-octanol, 2-methyl-1-butanol and an amino acid derivative have been used as optically active sources. However, the characteristics of the obtained materials are limited so long as the above optically active materials are used.

In recent years, in the field of the ferroelectric liquid crystal compounds, attempts have been vigorously made to synthesize the ferroelectric liquid crystal compounds from the following alcohols having a fluoroalkyl group substituted on an asymmetric carbon atom (c*), as optically active source (see, e.g., JP-A-64-3154, JP-A-1-316339, JP-A-1-316367, JP-A-1-316372, JP-A-2-225434 and JP-A-2-229128).

(1) $CF_3C^*H(OH)CH_2COOC_2H_5$ (2) $CF_3C^*H(OH)CH_2CH_2OC_2H_5$ (3) $CF_3C^*H(OH)CH_2CH_2CH_2OC_2H_5$ (4) $CF_3C^*H(OH)C_6H_{13}$ (5) $CF_3C^*H(OH)C_8H_{17}$ (6) $C_2F_5C^*H(OH)C_8H_{17}$

All of anti-ferroelectric liquid crystal compounds derived from the above alcohols give high spontaneous polarization and give also a relatively rapid response speed since they have a fluoroalkyl group having a high electronegativity substituted on the asymmetric carbon atom.

It is also known that, out of these alcohols, liquid crystals derived from (4) $CF_3C^*H(OH)C_6H_{13}$, (5) $CF_3C^*H(OH)C_8H_{17}$, (6) $C_2F_5C^*H(OH)C_8H_{17}$, etc., easily give liquid crystals having an anti-ferroelectric liquid crystal phase, and hence, these alcohols attract attention as particularly characteristic alcohols.

Further, with regard to the method of synthesizing the optically active alcohol of $CF_3C^*H(OH)(CH_2)_mOC_nH_{2n+1}$ in which m is an integer of 2 to 7 and n is an integer of 1 to 4, the present inventors made detailed studies of a novel method of producing the intended optically active alcohol having a high optical purity without using expensive ethyl trifluoroacetoacetate, and a liquid crystal compound derived therefrom, and as a result, found that there could be obtained an extremely useful anti-ferroelectric liquid crystal compound or a ferrielectric liquid crystal compound both of which were not known before (see JP-A-5-65486 and JP-A-8-337555).

However, it has been found that an anti-ferroelectric liquid crystal compound or a ferrielectric liquid crystal compound derived from the above optically active alcohol has the following problem.

(i) Tilt angle is small.

(ii) The upper limit temperature of an anti-ferroelectric phase or a ferrielectric phase is low.

(iii) Viscosity is high.

There is therefore demanded a novel optically active alcohol which can impart a liquid crystal compound with characteristics which can overcome the above problems.

A optically active secondary alcohol can be produced by various methods.

From the economical point of view, the use of an optically active compound as a starting material is not proper since the optically active compound is expensive.

A optically active secondary alcohol can be also produced by a method by asymmetric synthesis. For obtaining an optically active alcohol, for example, it is thinkable to prepare a corresponding ketone as a precursor and then, asymmetrically reduce the ketone in the presence of an asymmetrically reducing catalyst. In this case, however, the asymmetrically reducing catalyst is very expensive, a product having a high optical purity cannot always be obtained, and only either an R-configuration or an S-configuration optically active alcohol is obtained.

It is also thinkable to asymmetrically hydrolyze a proper ester which is a precursor for an optically active compound, such as an acetate. An enzyme can be used as an effective asymmetric hydrolysis agent. The asymmetric hydrolysis of the acetate with lipase has been proposed by Kitazume et al (see T. Kitazume et al., J. Org. 52, 3211 (1987), JP-A-2-282340).

According to Kitazume et al, the acetate of the formula, $CF_3CH(OCOCH_3)C_nH_{2n+1}$ (in which n is an integer of 4 to 8) is asymmetrically hydrolyzed in the presence of lipase MY in a phosphate buffer solution.

However, the capability of lipase MY for recognizing asymmetry is greatly dependent upon the chemical structure of a compound to be hydrolyzed, and the optical purity of obtained hydrolysis products considerably varies from 55 to 98 ee % depending upon their chemical structures as shown in Table 1 in the above literature by Kitazume et al.

The above results show that it is difficult to predict whether or not an intended compound can be effectively asymmetrically hydrolyzed and that it is found only after a reaction whether or not an intended alcohol having a high optical purity can be obtained.

Further, there is another serious problem in that the capability for asymmetry recognition is not at all exhibited when some kinds of substituents are present on an asymmetric carbon atom.

For example, while the lipase MY exhibits the remarkably high capability for asymmetry recognition in the asymmetric hydrolysis of $CF_3C^*H(OCOCH_3)(CH_2)_5OC_2H_5$, it does not show any asymmetry recognition for an ester of a secondary alcohol $CH_3CH(OCOCH_3)C_6H_{13}$ having a methyl group substituted on the asymmetric carbon atom.

In addition of the above-mentioned methods, a optically active secondary alcohol is also produced by a method in which a secondary racemic alcohol is asymmetrically trans-esterified in the presence of a proper enzyme to be optically resolved.

One example is a reaction of asymmetric trans-esterification of a secondary racemic alcohol in an organic solvent in the presence of a lipase (derived from porcine pancreas) (see A. M. Klibanov et al., J. Am. Chem. Soc. 1985, 107, 7072).

However, no lipase having high activity and high enantio-selectivity has been known. The asymmetric hydrolysis and the optical resolution by the asymmetric trans-esterification using an enzyme have an advantage in that both the R-configuration and S-configuration optical active compounds are easily obtained.

The present invention has been made in view of the above circumstances, and it is an object of the present invention to provide a novel optically active secondary alcohol having a trifluoromethyl group on an asymmetric carbon atom and having a fluorine-atom-substituted alkoxy group at a terminal, and a process for the advantageous production thereof.

Studies by the present inventors have revealed that the above object of the present invention is achieved by an R-configuration or S-configuration optically active alcohol of the formula (1),

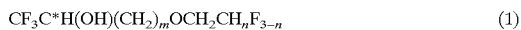

$$CF_3C^*H(OH)(CH_2)_mOCH_2CH_nF_{3-n} \quad (1)$$

wherein C* is an asymmetric carbon atom, m is an integer of 2 to 7, and n is an integer of 0 to 2.

The optically active alcohol of the above formula (1) in which m is 5 or n is 0 or 2 is preferred since it gives an anti-ferroelectric liquid crystal compound having excellent characteristics.

Further, according to the studies by the present inventors, a process for advantageously producing the optically active alcohol of the above formula (1) has been found. That is, according to the present invention, there is provided a process for the production of the optically active alcohol of the formula (1), which comprises the following steps (1) to (4).

In the step (1), a halogen compound of the formula (2) is converted to a Grignard reagent,

$$X(CH_2)_mOCH_2CH_nF_{3-n} \quad (2)$$

wherein m and n are defined as in the formula (1) [m and n in formulae to be described later also have the same meanings as those in the formula (1)], and X is a halogen atom other than a fluorine atom, and then the Grignard reagent is reacted with a trifluoroacetic acid metal salt of the formula (3) or (4),

$$CF_3COOM^1 \quad (3)$$
$$(CF_3COO)_2M^2 \quad (4)$$

wherein $M^1$ is Li, Na or K and $M^2$ is Mg or Ca, to form a ketone of the formula (5)

$$CF_3CO(CH_2)_mOCH_2CH_nF_{3-n} \quad (5).$$

In the step (2), the ketone of the formula (5) is reduced to form a racemic alcohol of the formula (6)

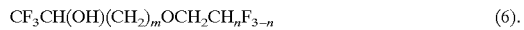

$$CF_3CH(OH)(CH_2)_mOCH_2CH_nF_{3-n} \quad (6).$$

In the step (3), the alcohol of the formula (6) is reacted with a halide or anhydride of an aliphatic carboxylic acid whose alkyl portion has 1 to 5 carbon atoms, to form an ester of the formula (7),

$$CF_3CH(OCOR)(CH_2)_mOCH_2CH_nF_{3-n} \quad (7)$$

wherein R is an alkyl group having 1 to 5 carbon atoms, and in the step (4), an asymmetric hydrolysis of the ester of the formula (7) is induced by lipase, then, after the completion of the hydrolysis, the reaction mixture is brought into contact with an organic solvent compatible with water to precipitate the lipase, the lipase is recovered by filtration, whereas an optically active alcohol and an optically active ester are separated from the filtrate.

In the production process of the present invention, the trifluoroacetic acid metal salt of the formula (3) or (4) to be reacted with the Grignard reagent in the step (1) is preferably used in the form of a tetrahydrofuran solution. Further, the reaction between the trifluoroacetic acid metal salt and the Grignard reagent in the step (1) is properly carried out at a temperature between 20° C. and 50° C.

In the step (2), it is preferred to an $NaBH_4$ aqueous solution containing sodium hydroxide as the reducing agent for reducing the ketone. The reduction of the ketone is preferably carried out at a temperature between 20° C. and 40° C.

In the step (3), the alkyl portion of the aliphatic carboxylic acid has 1 to 5 carbon atoms, preferably 1 to 3 carbon atoms. And, the halide or anhydride of the aliphatic carboxylic acid includes acetic acid chloride, propionic acid chloride, butyric acid chloride, acetic anhydride, propionic anhydride, and the like. The step (3) is properly carried out at a temperature between 60° C. and 90° C.

As a lipase used in the step (4), lipase derived from porcine pancreas is preferred, and lipase MY is particularly advantageously used. The lipase MY is commercially available, for example, from MEITO SANGYO CO., LTD and is easily obtained.

In the step (4), desirably, the asymmetric hydrolysis with lipase is carried out at a temperature between 20° C. and 40° C., and the amount of water used per mole of the ester is 20 to 50 mol.

Further, in the step (4), the reaction mixture after the asymmetric hydrolysis with the lipase is brought into contact with an organic solvent of which the amount is 5 to 20 times the amount of the water used for the asymmetric hydrolysis, to precipitate the lipase. The precipitated lipase is recovered by filtration. The recovered lipase is dried under reduced pressure and can be recycled in the step (4), and the optically active alcohol can be therefore more economically produced. The above organic solvent is preferably at least one member selected from the group consisting of acetone, methanol, ethanol and tetrahydrofuran. Further, the optically active ester separated in the step (4) can be converted to an optically active alcohol by hydrolyzing it by a known method per se.

EXAMPLES

The present invention will be explained in detail with reference to Examples hereinafter, while the present invention shall not be limited thereto.

Example 1

Preparation of R-(+)-7-(2'-Fluoroethoxy)-1,1,1-Trifluoro-Heptan-2-Ol (E1), Formula (1) in which m=5, n=2

(1) Preparation of 1-bromo-5-(2'-fluoroethoxy)-pentane;

20 Grams of 60% sodium hydride was added to 500 ml of anhydrous dimethylformamide under a nitrogen gas current, and the mixture was stirred with cooling with ice for 2 hours. To the reaction mixture was added 200 ml of a solution of 100 g of 1,5-dibromopentane in dimethylformamide so as to bring the reaction temperature to 20° C. or lower.

Then, the reaction mixture was stirred at room temperature for 15 hours, water was added, and the mixture was extracted with ether. An ether layer was washed with IN hydrochloric acid, then washed with water and, further, washed with a saturated sodium chloride aqueous solution. The ether layer was dried over anhydrous sodium sulfate, and then the ether was distilled off, to give 130 g of a crude product.

The crude product was purified by distillation, to collect a fraction having a boiling point of 90 to 95° C. (7 Torr).

The above fraction contained 60% of 1-bromo-5-(2'-fluoroethoxy)-pentane and others such as dibromopentane used as raw material and 1,5-bis(2'-fluoroethoxy)-pentane as a byproduct.

(2) Preparation of 7-(2'-fluoroethoxy)-1,1,1-trifluoro-heptan-2-ol;

6.5 Grams of metal magnesium was placed in a round-bottom flask, atmosphere in the flask was replaced with a nitrogen gas, and then 100 ml (milliliter) of dry tetrahydrofuran was added.

20 Grams (110 mmol, purity 60%) of the 1-bromo-5-(2'-fluoroethoxy)-pentane obtained in the above (1) was dissolved in 100 ml of the dry tetrahydrofuran, and the resultant solution was added dropwise so as to bring the reaction temperature to 40° C. or lower. The reaction mixture was aged for 1 hour, then, 200 g of magnesium bis(trifluoroacetate) (280 mmol, 35% tetrahydrofuran solution) was added dropwise so as to bring the reaction temperature to 50° C. or lower, and then the mixture was allowed to react at 50° C. for 2 hours.

After the completion of the reaction, 150 ml of 6 N hydrochloric acid was added dropwise, the mixture was stirred at room temperature for 2 hours, and an organic layer was separated. 28 Grams of an NaOH solution containing 12% of $NaBH_4$ was gradually added dropwise to the organic layer, and the mixture was stirred at room temperature for 3 hours. Then, water was added, and the mixture was extracted with ether.

An obtained ether layer was washed with 6 N hydrochloric acid and then washed with water until the ether layer became almost neutral, and further, the ether layer was washed with a saturated sodium chloride aqueous solution. The ether layer was dried over anhydrous sodium sulfate, and the ether was distilled off to give 25 g of a crude product. The crude product was purified by distillation (3 Torr, 90 to 95° C.) to give 12.2 g of an intended product (purity by gas chromatography analysis (GC purity) 72%).

(3) Preparation of 7-(2'-fluoroethoxy)-1,1,1-trifluoro-2-acetoxy-heptane;

10 Grams (98 mmol) of acetic anhydride and 10 g (130 mmol) of pyridine were added to 12.2 g (38 mmol, GC purity 72%) of the 7-(2'-fluoroethoxy)-1,1,1-trifluoro-heptan-2-ol obtained in the above (2), and then the mixture was stirred at room temperature for 30 hours. Then, 10 ml of water was added, and the mixture was stirred for 10 hours. Further, water was added, and the mixture was extracted with ether.

An obtained ether layer was washed with 6 N hydrochloric acid, then washed with water until it became almost neutral, and further, washed with a saturated sodium chloride aqueous solution. The ether layer was dried over anhydrous sodium sulfate, and the ether was distilled off to give 10 g of a crude product. The crude product was purified by distillation (2 Torr, 72 to 78° C.) to give 8.9 g of an intended product (GC purity 70%).

(4) Preparation of R-(+)-7-(2'-fluoroethoxy)-1,1,1-trifluoro-heptan-2-ol;

30 Grams of water and 8.2 g of lipase MY (supplied by MEITO SANGYO CO., LTD) were added to 6 g (22 mmol) of the acetyl compound obtained in the above (3), and the mixture was stirred at room temperature for 8 hours. Then, 150 ml of acetone was added, and the mixture was stirred for 1 hour. Precipitated lipase was separated by filtration, and then the acetone was distilled off.

To this resulting mixture was added water, and the mixture was extracted with ether. An ether layer was washed with water several times and, further, washed with a saturated sodium chloride aqueous solution. The ether layer was dried over anhydrous sodium sulfate, and then the ether was distilled off to give a crude product.

(5) The above crude product was purified by silica gel column chromatography to separate it into R-(+)-7-(2'-fluoroethoxy)-1,1,1-trifluoro-heptane-2-ol and S-(−)-7-(2'-fluoroethoxy)-2-acetoxy-1,1,1-trifluoro-heptane.

The yield of the R-(+)-7-(2'-fluoroethoxy)-1,1,1-trifluoro-heptane-2-ol was 2.2 g. On the other hand, the S-(−)-7-(2'-fluoroethoxy)-2-acetoxy-1,1,1-trifluoro-heptane was hydrolyzed to give S-(−)-7-(2'-fluoroethoxy)-1,1,1-trifluoro-heptane-2-ol.

Table 1 shows NMR data of the R-(+) configuration compound, and Table 2 shows the specific rotatory power and optical purity thereof.

The optical purity and the specific rotatory power were determined as follows.

The R-(+) configuration optically active alcohol obtained in the above (5) was converted to an acetate with pyridine/acetic anhydride. The resultant acetate was analyzed with a gas chromatograph (CP Cyclodex β236M) used for the analysis of optically active materials, and the purity was determined on the basis of a peak area ratio of two enanthiomers.

Further, chloroform was used as a solvent and an optical rotation meter was used to determine the specific rotatory power.

Example 2

Preparation of R-(+)-7-(2',2',2'-Trifluoroethoxy)-1,1,1-Trifluoro-Heptane-2-Ol (E2), Formula (1) in which m=5, n=0

An intended product was synthesized in the same manner as in Example 1 except that 2-fluoroethanol was replaced with 2-trifluoroethanol.

Tables 1 and 2 show the NMR data, specific rotatory power and optical purity of the obtained intended products.

TABLE 1

| Example No. | Compound and proton number | Chemical shift (ppm) | | | |
|---|---|---|---|---|---|
| 1 (E1) | $CF_3C^*H(OH)(CH_2)_5OCH_2CH_2F$<br>   1   2            3   4 | 3.9 | 2.1 | 3.6 | 4.6 |
| 2 (E2) | $CF_3C^*H(OH)(CH_2)_5OCH_2CF_3$<br>   1   2            3 | 3.9 | 2.1 | 3.6 | |

TABLE 2

| Example No. | Chemical structure | Optical purity | Specific rotatory power*1 |
|---|---|---|---|
| 1 (E1) | $CF_3C^*H(OH)(CH_2)_5OCH_2CH_2F$ | >95% ee | +20.9° |
| 2 (E2) | $CF_3C^*H(OH)(CH_2)_5OCH_2CF_3$ | >95% ee | +17.7° |

*1: Measured with sodium D ray at 29° C.

The present invention provides a novel optically active secondary alcohol having a trifluoromethyl group on an asymmetric carbon atom and a fluoroalkoxy group at a terminal, and a process for producing them economically and easily.

We claim:

1. An R-configuration or S-configuration optically active alcohol of the formula (1), $$CF_3C^*H(OH)(CH_2)_mOCH_2CH_nF_{3-n} \qquad (1)$$

wherein C* is an asymmetric carbon atom, m is an integer of 2 to 7, and n is an integer of 0 to 2.

2. The optically active alcohol of claim 1, which has the formula (1) in which m is 5.

3. The optically active alcohol of claim 1 or 2, which has the formula (1) in which n is 0 or 2.

4. A process for the production of the optically active alcohol of the formula (1)

$$CF_3C^*H(OH)(CH_2)_mOCH_2CH_nF_{3-n} \qquad (1)$$

wherein

C* is an asymmetric carbon atom, m is an integer of 2 to 7, and n is an integer of 0 to 2, which comprises the following steps (1) to (4), step (1): converting a halogen compound of the formula (2) to a Grignard reagent, $$X(CH_2)_mOCH_2CH_nF_{3-n} \qquad (2)$$

wherein m and n are defined as in the formula (1) [m and n in formulae to be described later also have the same meanings as those in the formula (1)], and X is a halogen atom other than a fluorine atom, and then reacting the Grignard reagent with a trifluoroacetic acid metal salt of the formula (3) or (4), $$CF_3COOM^1 \qquad (3)$$

$$(CF_3COO)_2M^2 \qquad (4)$$

wherein $M^1$ is Li, Na or K and $M^2$ is Mg or Ca, to form a ketone of the formula (5), $$CF_3CO\,(CH_2)_mOCH_2CH_nF_{3-n} \qquad (5)$$

step (2): reducing the ketone of the formula (5) to form a racemic alcohol of the formula (6), $$CH_3CH(OH)(CH_2)_mOCH_2CH_nF_{3-n} \qquad (6)$$

step (3): reacting the alcohol of the formula (6) with a halide or anhydride of an aliphatic carboxylic acid whose alkyl portion has 1 to 5 carbon atoms, to form an ester of the formula (7), $$CF_3CH(OCOR)(CH_2)_mOCH_2CH_nF_{3-n} \qquad (7)$$

wherein R is an alkyl group having 1 to 5 carbon atoms, and step (4): inducing an asymmetyric hydrolysis of the ester of the formula (7) with lipase, then, after the completion of the hydrolysis, bringing the reaction mixture into contact with an organic solvent compatible with water to precipitate the lipase, recovering the lipase by filtration, and separating an optically active alcohol and an optically active ester from the filtrate.

5. The process of claim 4, wherein the trifluoroacetic acid metal salt to be reacted with the Grignard reagent in the step (1) is used in the form of a tetrahydrofuran solution.

6. The process of claim 4, wherein the step (2) uses an $NaBH_4$ aqueous solution containing sodium hydroxide used as a reducing agent for the reduction of the ketone.

7. The process of claim 4, wherein the asymmetric hydrolysis reaction with the lipase in the step (4) is carried out at a temperature between 20° C. and 40° C.

8. The process of claim 4, wherein the asymmetric hydrolysis with the lipase in the step (4) uses water in an amount 20 to 50 times the molar amount of the ester.

9. The process of claim 4, wherein a reaction mixture from the asymmetric hydrolysis reaction with the lipase is brought into contact with an organic solvent in an amount 5 to 20 times the amount of water used for the asymmetric hydrolysis, to precipitate the lipase, and the precipitated lipase is recovered by filtration, dried under reduced pressure and recycled in the step (4).

10. The process of claim 4, wherein the organic solvent is at least one member selected from the group consisting of acetone, methanol, ethanol and tetrahydrofuran.

* * * * *